United States Patent [19]

Smith

[11] Patent Number: 4,892,409

[45] Date of Patent: Jan. 9, 1990

[54] PHOTOMETRIC APPARATUS FOR MULTIWELL PLATES HAVING A POSITIONABLE LENS ASSEMBLY

[76] Inventor: Harry F. Smith, 7 Fern Lake, Newtown, Conn. 06470

[21] Appl. No.: 218,874

[22] Filed: Jul. 14, 1988

[51] Int. Cl.$^4$ .................. G01N 21/31; G01N 21/84
[52] U.S. Cl. ................................. 356/414; 250/228; 250/576; 356/236; 356/440
[58] Field of Search .............. 356/236, 436, 440, 409, 356/414; 250/576, 228

[56] References Cited

U.S. PATENT DOCUMENTS

| | | | |
|---|---|---|---|
| 3,627,431 | 12/1971 | Komarniski | 356/409 |
| 3,827,808 | 8/1974 | Cho | 356/236 X |
| 4,027,979 | 6/1977 | Komarniski | 356/414 X |
| 4,448,534 | 5/1984 | Wertz et al. | 356/436 X |

OTHER PUBLICATIONS

A product brochure entitled "Integrating Spheres", copyright 1988 by Labsphere, Inc., North Sutton, NH.
A product brochure entitled "Vmax Kinetic Microplate Reader", undated, by Molecular Devices Corporation, Palo Alto, CA.
A product brochure entitled "Model EL309 Automated EIA Plate Reader User's Manual", undated, by Bio—Tex Instruments, Burlington, VT.

Primary Examiner—Vincent P. McGraw

[57] ABSTRACT

The invention relates to photometric apparatus and method for determining a characteristic of individual ones of a plurality of samples contained within a plurality of sample chambers. The photometric apparatus includes an enclosure; a substantially uniform source of radiation coupled to the enclosure such that a plurality of sample chambers, disposed within the enclosure, are simultaneously illuminated by the uniform source; and apparatus for detecting an amount of radiation which is transmitted through individual ones of the sample chambers, the detecting apparatus having an output signal having a magnitude which is a function of the amount of radiation which is transmitted through an individual one of the sample chambers. The substantially uniform source of radiation may include at least one source of radiation having an output comprising wavelengths within a first range of wavelengths and an optically integrating sphere having a radiation input port coupled to the output of the source of radiation and a radiation output port coupled to the enclosure. The photometric apparatus may further include radiation directing devices interposed between the radiation output port and the plurality of sample chambers for simultaneously directing radiation emanating from the output port into each of the sample chambers. The directed radiation may be either focussed or collimated.

24 Claims, 3 Drawing Sheets

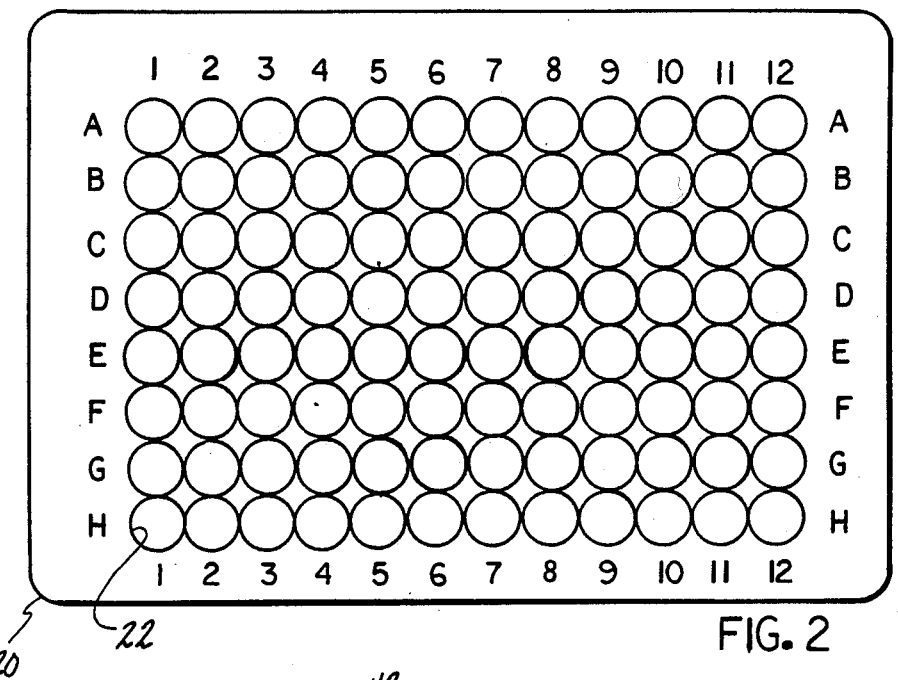
FIG. 2
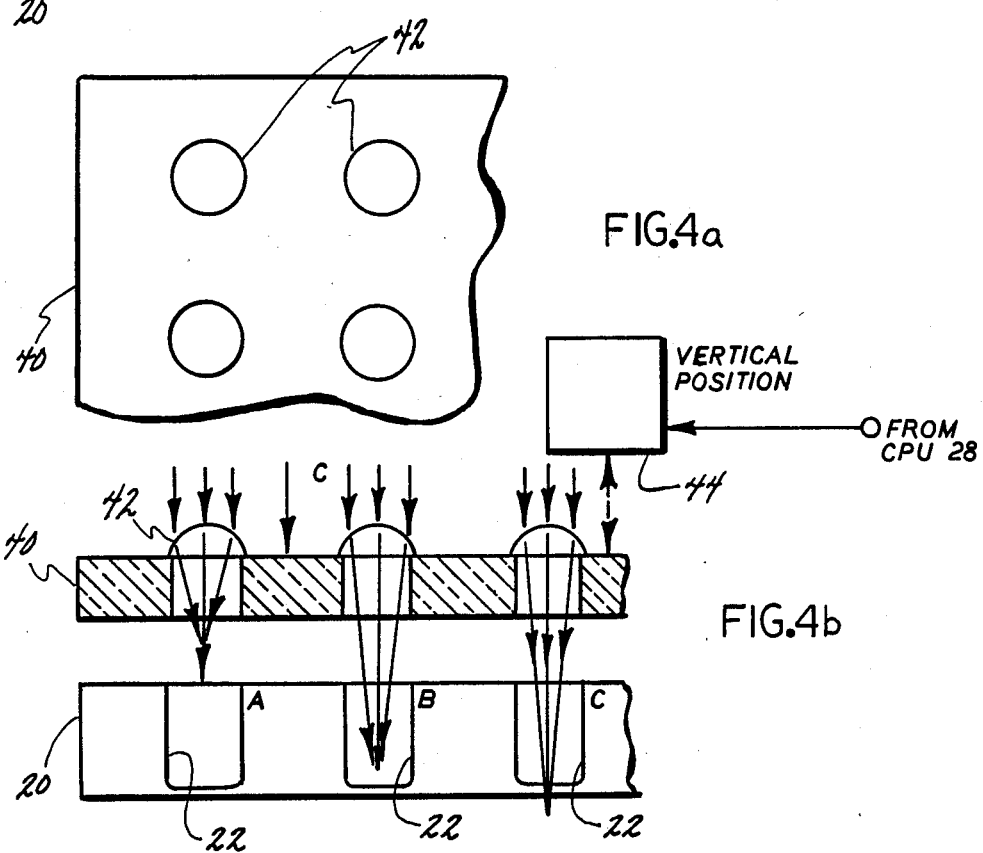
FIG. 4a
FIG. 4b

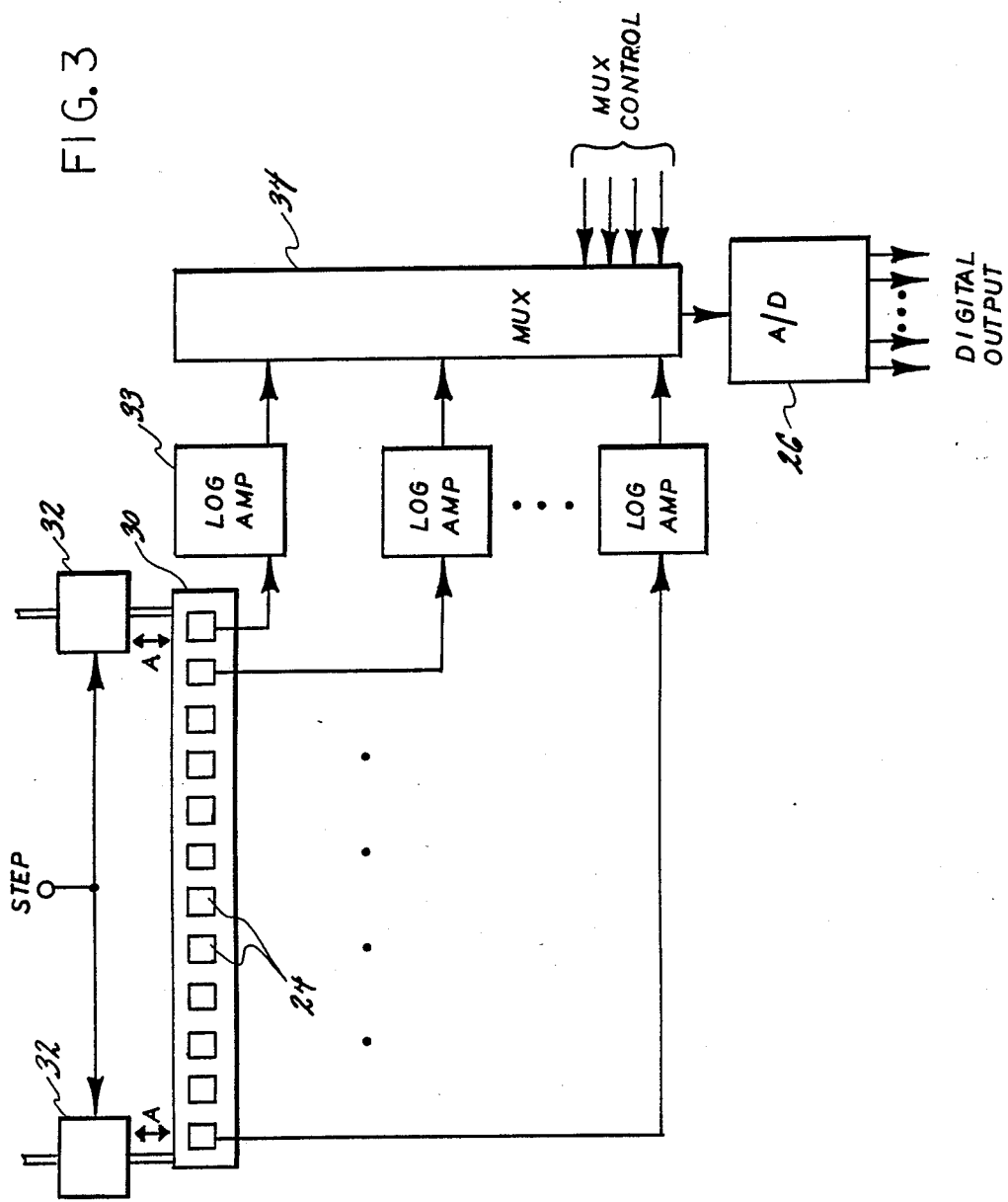

PHOTOMETRIC APPARATUS FOR MULTIWELL PLATES HAVING A POSITIONABLE LENS ASSEMBLY

FIELD OF THE INVENTION

This invention relates generally to photometric devices and, in particular, to a high speed spectrophotometer having a substantially Lambertian source of radiation for uniformly illuminating a sample plate having a plurality of sample-containing wells.

BACKGROUND OF THE INVENTION

Spectrophotometers operable for performing enzyme-linked immunosorbent assays (ELISA) are widely known and used in the pharmaceutical and biotechnology industries. Of special interest are such spectrophotometers adapted for performing a kinetic analysis of the rate of change of optical density (OD) within a sample. Typically a plurality of samples are provided within a plurality of wells formed within a plate, also known as a microplate. A source of radiation is provided for illuminating one or more of the wells and the transmission of radiation through each of the samples is repetitively measured, the amount of transmission being indicative of the OD of the sample. The OD is in turn indicative of the enzyme activity of the sample.

One consideration with such kinetic analysis spectrophotometers is the speed at which each of the sample wells within a microplate is measured. In that an initially linear OD excursion may occur in a relatively short period of time, a sufficient number of readings must be acquired rapidly in order to characterize the slope of the reaction. The individual sample acquisition rate also directly influences the amount of time required to read an entire microplate, which may contain 96 sample wells arranged in a two dimensional array. In that several dozen or even hundreds of microplates may be required to be sequentially read by the spectrophotometer, the amount of time required to acquire data from a single plate is of importance.

Another consideration is the consistency of measurement accuracy of wells on the same plate in that certain of the wells may contain a reference sample against which other wells are measured. Measurement consistency is a function at least of the uniformity of the illumination from well to well.

SUMMARY OF THE INVENTION

In accordance with the invention there is provided apparatus and method for performing a photometric analysis with a sample holder having a plurality of sample chambers by providing a highly uniform, essentially Lambertian radiation source for simultaneously illuminating the plurality of sample chambers.

In accordance with one aspect of the invention there is disclosed photometric apparatus for determining a characteristic of individual ones of a plurality of samples contained within a plurality of sample chambers. The photometric apparatus comprises an enclosure; means for providing a substantially uniform source of radiation to the enclosure such that a plurality of sample chambers, disposed within the enclosure, are simultaneously illuminated by the uniform source; and means for detecting an amount of radiation, if any, which is transmitted through individual ones of the sample chambers, the detecting means having an output signal having a magnitude which is a function of the amount of radiation, if any, which is transmitted through an individual one of the sample chambers. The substantially uniform source of radiation includes at least one source of radiation having an output comprising wavelengths within a first range of wavelengths and an optically integrating sphere having a radiation input port coupled to the output of the source of radiation and a radiation output port coupled to the enclosure. The photometric apparatus may further include radiation directing means interposed between the radiation output port and the plurality of sample chambers for simultaneously directing radiation emanating from the output port into each of the sample chambers.

In accordance with a method of the invention there is disclosed a method of determining an optical density of individual ones of a plurality of samples contained within a plurality of sample chambers. The method includes the steps of providing a plurality of sample chambers within an enclosure; illuminating the plurality of sample wells with a uniform, substantially Lambertian source of radiation within a predetermined range of wavelengths; and detecting an amount of radiation which is transmitted through individual ones of the sample chambers, the detected radiation being a function of the optical density of a sample within a sample chamber. The step of illuminating may be accomplished by the steps of providing at least one source of radiation having an output comprising wavelengths within a first range of wavelengths; and providing an optically integrating sphere having a radiation input port coupled to the output of the source of radiation and a radiation output port coupled to the enclosure. The method further encompasses a step of directing radiation emanating from the radiation output port into each of the sample wells, such as by focussing or collimating the radiation with a plurality of lens elements individual ones of which are interposed between a sample well and the uniform source of radiation.

BRIEF DESCRIPTION OF THE DRAWING

The foregoing and other aspects of the invention will be made more apparent in the ensuing Detailed Description of the Invention read in conjunction with the attached Drawing wherein:

FIG. 2 is a top view of a typical 96-well microplate;

FIG. 3 is a block diagram which illustrates apparatus for measuring the optical density of a plurality of wells within a row of the microplate of FIGS. 2;

FIG. 4a shows a top view of a portion of focussing device and FIG. 4b is a side, cut-away view of the device of FIG. 4a shown positioned relative to a microplate and coupled to a vertical positioner for adjusting the focal point.

DETAILED DESCRIPTION OF THE INVENTION

Figure 1:
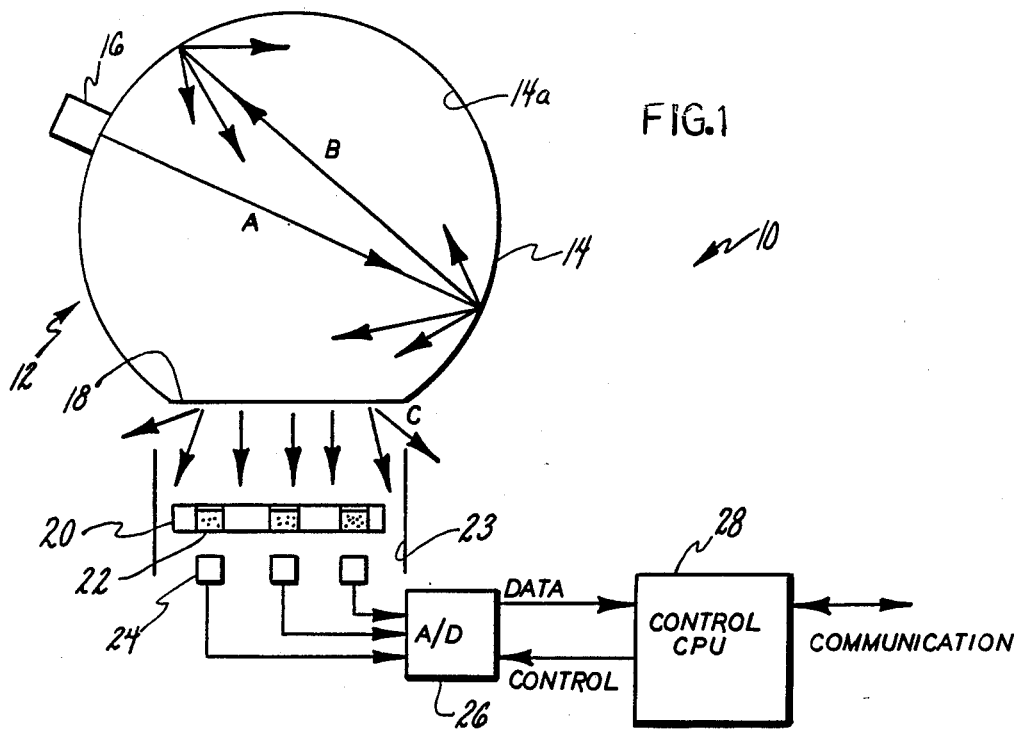
FIG. 1 is a simplified block diagram of a photometric system 10 constructed in accordance with the invention.

Referring now to FIG. 1 there is shown, in accordance with a method and apparatus of the invention, a photometric system 10. System 10 comprises an optical stage which includes a uniform, substantially Lambertian, radiation source 12 which in turn may comprise an integrating sphere 14 having at least one radiation source 16 coupled to an input port thereof. Radiation source 16 may be a tungsten-halogen bulb having output radiation in the ultraviolet (UV) region of the electromagnetic spectrum. The interior of the sphere 14 is coated with a reflective coating 14a which, in conjunction with the geometry of the sphere 14, collects the UV radiation emitted by the source 16 and causes numerous diffuse reflections, as illustrated by the beams A and B. Radiation emanating from an output port 18 of the sphere 14 is indicated by the arrows C. A plane of the exit port 18 is characterized as being a plane of constant irradiance or illuminance. That is, the radiance is constant over the plane of the exit port 18 and is substantially independent of viewing angle. The plane of the exit port 18 may be characterized as being a substantially Lambertian source.

Source 16 may also comprise a filter wheel 16a or some other multi-filter device for selecting a relatively narrow range, such as a 10 nanometer range, of wavelengths for application to the sphere 14. For example, typical wavelengths used for such measurements may include wavelengths within the range of approximately 300 to 750 nanometers. Integrating spheres characterized for operation at such wavelengths are commercially available. For example, integrating spheres manufactured by Labsphere, Inc. of North Sutton, N.H. are characterized as having internal coating 14a reflectance values of approximately 0.95 to 0.98 over the range of wavelengths of 300 to 800 nanometers.

Disposed to receive the output radiation C is a sample holder or plate 20 having a plurality of sample wells 22 contained therein. The plate 20 may be inserted either manually or automatically into an enclosure 23 in order to minimize the effects of ambient illumination. A number of the wells 22, during the operation of the system 10, contain a liquid phase sample through which the radiation C is directed. One or more detectors 24 are disposed relative to the sample wells 22 for detecting the amount of radiation C which is transmitted through the wells 22, the amount of transmitted radiation being a function of the optical density (OD) of the sample. The detectors 24 may be UV-enhanced silicon photodetectors having an output coupled to an amplifier, such as a logarithmic amplifier. The outputs of detectors 24 are coupled to the input of a measurement system which may comprise signal conditioning and processing circuitry such as an analog to digital (A/D) converter 26 having digital outputs which are supplied to a control means such as a control CPU 28. Control CPU 28 may also have a plurality of output control lines for controlling the operation of the A/D converter 26. Control CPU 28 may also be provided with a communication signal bus, such as an RS-232 serial bus, for communicating with another computer wherein the data acquired from the detectors 24 is analyzed and displayed. The communication port may also be coupled to a suitable output means such as a printer or a CRT display device.

As can be seen in FIG. 1, and in accordance with the invention, the entire plate 20 is illuminated by the substantially uniform, Lambertian source of illumination which is coupled to the enclosure 23. That is, each of the sample wells is subjected simultaneously to an essentially equal amount of input radiation flux.

Although the invention is described herein in the context of an optically integrating sphere any radiation source which is capable of providing a substantially uniform source of radiation to the enclosure 23 may be employed.

Referring to FIG. 2 there is shown a typical sample plate 20 which can be seen to be comprised of 96 sample wells 22 which are arranged in eight rows (A-H) and twelve columns (1-12). Of course, the use of the invention is also applicable to strip wells and other configurations of wells within a sample plate. The sample plate 20 is usually comprised of an optically transparent plastic medium. During the measurement of samples contained within wells 22 several of the wells may be left empty in order to calibrate the measurement for the amount of radiation absorption due to the material of the plate 20 itself. Certain of the wells may also contain a sample of known OD as an aid in calibration. For certain applications the bottom of each well may comprise a layer of filter material. An initial reading on air may also be accomplished in order to calibrate the detectors, these measurements being stored by CPU 28 and applied as correction factors to subsequently acquired readings.

Inasmuch as it is one object of the invention to provide for a high speed photometric system there is illustrated in FIG. 3 a plurality of photodetectors 24 linearly arranged on a substrate or carrier 30. Although twelve photodetectors 24 are shown in FIG. 3 for scanning the plate 20 in a row at a time fashion it can be appreciated that the carrier 30 may include 8 photodetectors for scanning the plate in a column by column fashion. Coupled to carrier 30 is shown a linear translation means such as a pair of linear actuators which may comprise stepping motors 32, the operation of which is controlled by a STEP input signal. The STEP signal is typically provided from the control CPU 28 in order to synchronize the linear movement, indicated by the arrows A, of the photodetectors 24 relative to the plate 20 with the operation of the signal measurement circuitry. An output of each of the photodetectors may be applied to an associated LOG AMP 32 the outputs of which are applied to an analog multiplexer (MUX) 34. MUX 34 will typically have a number of analog inputs at least equal to the number of photodetectors 24. A digital MUX CONTROL input is provided, again typically from the control CPU 28, to select one of the analog inputs for application to the analog to digital converter A/D 26. Of course, any suitable converter means may be employed, such as a voltage to frequency (V/F) device. Also, the MUX 34 may be an integral part of the converter, that is the MUX may be integrated within the same circuit package as the A/D or V/F.

Figure 5:
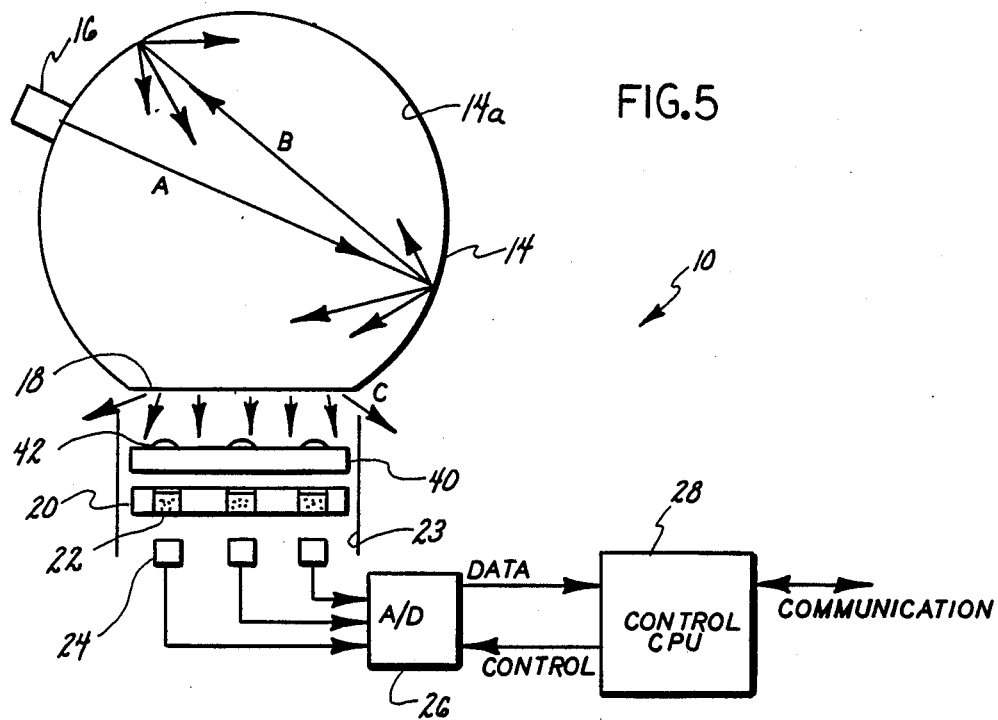
FIG. 5 is the simplified block diagram of the system 10 of FIG. 1 including the focussing device of FIGS. 4a and 4b.

For some applications it may be desirable to increase the radiation flux density through each of the wells in order to provide for the determination of a wider range of optical densities. The invention accommodates this feature by providing the optical stage with a radiation directing means, such as an array of plano-convex lenses 42 individual ones of which are interposed between each of the sample wells 22 and the uniform source of radiation C. As illustrated in FIGS. 4a and 4b each of the lenses 42 may be disposed upon a common substrate 42, the substrate 40 having a plurality of openings made therethrough in registration with individual ones of the wells 22 when the plate 20 is inserted within the enclosure 23. As shown in FIG. 5 the lenses 42 are interposed between the source C and the plate 20. Each of the lenses 42 may be individually mounted on the substrate 40 or the substrate 40 may be integral with each of the lenses 42, each of the lenses 42 being a convex region upon the surface of the substrate 40. Other types of focussing lens, such as convex and aspheric lens, may also be provided.

If the lens elements are focussing lenses the focal length of the lenses 42 is determined to focus the radiation at a desired point relative to the sample within the wells 22. As shown in well A of FIG. 4b the lens may focus the radiation at a point above the well or, as in well B, within the well or, in well C, at a point below the well, such as at a point coincident with the surface of an underlying photodetector. If it is desired to provide for significant optical isolation between individual wells the substrate 40 may be made reflective or optically black in the region between lenses 42. Furthermore, the substrate 40 may be coupled to a manual or automatic positioning means 44 for adjusting the distance between the substrate 40 and the plate 20, thereby achieving a focal point best suited for a given sample density or some other sample characteristic.

If desired, a lens type may be selected which collimates the output of the sphere 14 such that each sample well is uniformly illuminated by a collimated radiation beam which is directed therethrough.

It can be appreciated that the photometric device constructed in accordance with the invention is operable for providing measurements over a 96 well sample plate in a brief period of time. Inasmuch as the entire plate is illuminated simultaneously with a uniform source of radiation the need to provide apparatus, such as fiber optic conductors, to individually illuminate a well or a subset of wells is eliminated. Furthermore, the Lambertian nature of the source provides for each of the wells being illuminated with a substantially equal amount of radiant flux. This uniform illumination enhances the measurement accuracy and uniformity across the plate 20. Furthermore, it can be appreciated that the provision of multiple photodetectors which are scanned across the plate provides for a number of readings to be accomplished in a short period of time. That is, and referring to FIG. 3, an entire row of 12 wells may be read without repositioning the photodetectors. The time between successive readings within a single row or column is essentially equal to the time required for the A/D conversion to be accomplished. As is well known, each conversion may be accomplished in tens of microseconds or even less. Of course, when positioning the photodetectors to a desired row it may be necessary to provide sufficient time, before making the first measurement, for the photodetectors output to stabilize; this amount of time being a function of the response time of the photodetector to a change in incident radiation. This response time may be approximately 100 milliseconds, depending upon the type of photodetector employed. Also, due to the relatively small distance between adjacent rows or columns, the carrier 30 may be positioned from one row or column to another also in a relatively brief period of time, for example 100 milliseconds. After repositioning the carrier 30 to a new row or column the time allocated for the response time of the photodetectors may also be used to allow the mechanical motion of the carrier 30 to be damped, resulting in an improvement in measuring accuracy.

Although there has been shown apparatus for translating the photodetectors while the plate 20 remains fixed it should be realized that the linear array of photodetectors may be fixed and the plate translated relative to the fixed array.

It can also be appreciated that another linear array of photodetectors could be provided at, for example, the opposite edge of the plate such that during the operation of the system 10 the two linear arrays approach one another in a direction towards the center of the plate 20, each linear array acquiring data from four rows of wells. This second array of photodetectors also preferably includes associated circuitry such as shown in FIG. 3. That is, the second array is coupled to associated log amplifiers, A/D, and possibly a second control CPU. Of course, the most rapid method of reading all 96 wells would be to provide an array of fixed, individual photodetectors for simultaneously reading each well. However, the cost associated with this number of photodetectors may be prohibitive for most applications.

It should be realized that what has been described above is an illustrative embodiment of the invention and that modifications of this illustrative embodiment may occur to those having skill in this art. For example, although the sphere 14 has been shown to be disposed vertically above the sample wells it is within the scope of the invention to provide the sphere 14 below the wells such that the output of the sphere is directed upwards through the bottom of the wells, the detectors being positioned above the wells. Also, any desired type of signal conditioning apparatus may be coupled to the output of the detectors, such as sample and hold amplifiers. In this regard it is within the scope of the invention to provide a modulated, such as a chopped, radiation output from the source 12, such as by modulating the source 16. If a modulated source is employed the signal conditioning apparatus may further include demodulating electronics. Thus it should be apparent that the invention should not be construed to be limited to only the embodiments disclosed above but should instead be considered to be limited only by the scope and breadth of the following claims.

What is claimed is:

1. A photometric apparatus for determining a characteristic of individual ones of a plurality of samples contained within a plurality of sample chambers, comprising:

an enclosure;
means for providing a substantially uniform source of radiation to said enclosure such that a plurality of sample chambers, disposed within said enclosure, are simultaneously illuminated by said uniform source means;
optical lens means, interposed between said uniform source providing means and the plurality of sample chambers, for directing radiation emanating from said substantially uniform source of radiation simultaneously into each of the sample chambers;
means, coupled to said optical lens means, for controllably positioning said optical lens means relative to the sample chambers; and
means for detecting an amount of radiation, if any, that is transmitted through individual ones of the sample chambers, said detecting means having an output signal having a magnitude which is a function of the amount of radiation, if any, which is transmitted through an individual one of the sample chambers.

2. A photometric apparatus as set forth in claim 1 wherein said source providing means comprises:

at least one source of radiation having an output comprising wavelengths within a first range of wavelengths; and
an optically integrating sphere having a radiation input port coupled to the output of said source of radiation and a radiation output port coupled to said enclosure.

3. A photometric apparatus as set forth in claim 1 wherein said optical lens means comprises a plurality of lens means individual ones of which are disposed upon a common substrate, said substrate being coupled to said positioning means.

4. A photometric apparatus as set forth in claim 2 wherein said first range of wavelengths is approximately 300 nanometers to approximately 800 nanometers.

5. A photometric apparatus as set forth in claim 4 and further comprising wavelength selection means interposed between said source of radiation and said input port for selecting a second range of wavelengths for input to said input port, said second range of wavelengths being substantially narrower than said first range of wavelengths.

6. A photometric apparatus as set forth in claim 1 wherein said optical lens means comprises a plurality of focussing lenses individual ones of which are supported upon a common substrate, said substrate being coupled to said positioning means for being positioned thereby.

7. A photometric apparatus as set forth in claim 1 wherein said optical lens means comprises a plurality of collimating lenses individual ones of which are supported upon a common substrate, said substrate being coupled to said positioning means for being positioned thereby.

8. A spectrophotometer for determining an optical density of individual ones of a plurality of samples contained within a plurality of sample chambers, comprising:
   an enclosure;
   means for providing a uniform source of radiation to said enclosure such that a plurality of sample containing chambers, disposed within said enclosure, are simultaneously illuminated by said uniform source;
   optical lens means comprising a plurality of lenses supported by a common substrate and interposed between said uniform source providing means and the plurality of sample chambers for directing radiation emanating from said uniform source providing means simultaneously into each of the sample containing chambers;
   positioning means coupled to said substrate for controllably positioning said plurality of lenses relative to the sample containing chambers; and
   means for detecting an amount of radiation, if any, which is transmitted through individual ones of the sample containing chambers, said detecting means having an output signal having a magnitude that is a function of the amount of radiation, if any, which is transmitted through an individual one of said sample containing chambers.

9. A spectrophotometer as set forth in claim 8 wherein said source providing means comprises:
   at least one source of radiation having an output comprising wavelengths within a first range of wavelengths; and
   an optically integrating sphere having a radiation input port coupled to the output of said source of radiation and a radiation output port coupled to said enclosure.

10. A spectrophotometer as set forth in claim 9 wherein said first range of wavelengths is approximately 300 nanometers to approximately 800 nanometers.

11. A spectrophotometer as set forth in claim 10 and further comprising wavelength filter means interposed between said source of radiation and said input port for selecting a second range of wavelengths for input to said input port, said second range of wavelengths being substantially narrower than said first range of wavelengths.

12. A spectrophotometer as set forth in claim 8 wherein said optical lens means comprises a plurality of focussing lenses individual ones of which are supported by said common substrate.

13. A spectrophotometer as set forth in claim 8 wherein said optical lens means comprises a plurality of discrete lenses individual ones of which are integrally formed with said substrate such that, when said substrate is interposed between said uniform source providing means and said sample containing chambers, individual ones of said discrete lenses are substantially in registration with individual ones of said sample containing chambers.

14. A spectrophotometer for determining an optical density of individual ones of a plurality of samples contained within a plurality of sample chambers, comprising:
   an enclosure;
   at least one source of radiation having an output comprising wavelengths within a first range of wavelengths;
   an optically integrating sphere having a radiation input port coupled to the output of said source of radiation, said optically integrating sphere further having a radiation output port coupled to said enclosure for providing a uniform, substantially Lambertian source of radiation to said enclosure such that a plurality of sample chambers, disposed within said enclosure, are simultaneously illuminated by said uniform source; and
   optical lens means, interposed between said uniform source providing means and the plurality of sample chambers, for directing radiation emanating from said radiation output port simultaneously into each of the sample chambers;
   means, coupled to said optical lens means, for controllably positioning said optical lens means relative to the sample chambers; and
   means comprising at least one photodetector for detecting an amount of radiation, if any, which is transmitted through individual ones of said sample chambers, said at least one photodetector having an output signal having a magnitude which is a function of the amount of radiation, if any, which is transmitted through an individual one of said sample chambers.

15. A spectrophotometer as set forth in claim 14 wherein said detecting means comprises a plurality of photodetectors each of which has an output signal having a magnitude that is a function of the amount of radiation transmitted through a sample chamber.

16. A spectrophotometer as set forth in claim 15 and further comprising data processing means coupled to said photodetector output signals.

17. A method of determining an optical density of individual ones of a plurality of samples contained within a plurality of sample chambers, comprising the steps of:

providing a plurality of sample chambers within an enclosure;

illuminating the plurality of sample wells with a uniform source of radiation having wavelengths within a predetermined range of wavelengths;

the step of illuminating including a step of passing the radiation through a plurality of lens means coupled to a common substrate interposed between the source and the sample chambers, the step of illuminating including a further step of positioning the substrate relative to the sample chambers to achieve a desired degree of illumination thereof; and detecting an amount of radiation, if any, which is transmitted through individual ones of the sample chambers, the detected radiation being a function at least of the optical density of a sample within a sample chamber.

18. A method as set forth in claim 17 wherein the step of illuminating is accomplished by the steps of:

providing at least one source of radiation having an output comprising wavelengths within a first range of wavelengths; and providing an optically integrating sphere having a radiation input port coupled to the output of the source of radiation and a radiation output port coupled to the enclosure.

19. A method as set forth in claim 17 wherein the predetermined range of wavelengths is approximately 300 nanometers to approximately 800 nanometers.

20. A method as set forth in claim 19 wherein the step of illuminating includes a step of selectively filtering the output of the source of radiation to provide the predetermined range of wavelengths.

21. A method as set forth in claim 17 wherein the step of passing includes a step of focussing the radiation passing through each of the lens means.

22. A method as set forth in claim 17 wherein the step of passing includes a step of collimating the radiation passing through each of the lens means.

23. An optical stage for a photometric apparatus, the photometric apparatus being of the type for determining a characteristic of a plurality of samples contained within a plurality of sample wells within a common sample well carrier, said optical stage comprising:

an enclosure for containing a sample carrier having a plurality of sample chambers;

a source of radiation having a first radiation output with wavelengths within a predetermined range of wavelengths;

means, optically coupled to said first radiation output, for diffusing the first radiation output of said source of radiation, said diffusing means having a second radiation output coupled to said enclosure for simultaneously illuminating substantially all of a plurality of sample chambers contained therein;

optical lens means, interposed between said diffusing means and the plurality of sample chambers, for directing radiation emanating from said diffusing means simultaneously into each of the sample chambers; and means, coupled to said optical lens means, for controllably positioning said optical lens means relative to the sample chambers.

24. An optical stage as set forth in claim 23 wherein said diffusing means comprises an optically integrating sphere having at least one input port and at least one output port, the input port being coupled to the source of radiation and the output port being coupled to said enclosure.

* * * * *